United States Patent [19]

Goldstein et al.

[11] Patent Number: 4,977,094

[45] Date of Patent: Dec. 11, 1990

[54] PROCESS FOR MONITORING THE QUALITY OF WATER

[75] Inventors: Arthur J. Goldstein, Weston; Edgardo J. Parsi, Lexington, both of Mass.

[73] Assignee: Ionics, Incorporated, Watertown, Mass.

[21] Appl. No.: 426,614

[22] Filed: Oct. 23, 1989

Related U.S. Application Data

[62] Division of Ser. No. 138,757, Dec. 28, 1987, Pat. No. 4,940,667.

[51] Int. Cl.$^5$ .............................................. G01N 1/18
[52] U.S. Cl. ...................................... 436/157; 436/38; 436/150; 422/78
[58] Field of Search ................. 436/38, 143, 150, 157, 436/181; 422/76, 78

[56] References Cited

U.S. PATENT DOCUMENTS

| | | | |
|---|---|---|---|
| 2,046,583 | 7/1936 | Rummel | 436/38 |
| 3,158,444 | 11/1964 | Larson et al. | 436/38 |
| 3,904,365 | 9/1975 | Larson et al. | 436/150 |
| 4,472,354 | 9/1984 | Passell et al. | 436/38 |
| 4,622,306 | 11/1986 | Düve | 436/38 |

*Primary Examiner*—Robert J. Warden
*Assistant Examiner*—Lyle Alfandary-Alexander
*Attorney, Agent, or Firm*—Norman E. Saliba

[57] ABSTRACT

A process is disclosed for monitoring the quality of water, said process comprising a first heated zone, means for introducing at least a portion of said water into said first heated zone, means for gently evaporating at least part of the water in the first heated zone and passing the vapor into and through a second heated zone, means for maintaining the temperature of said second heated zone in the range of from about 450° to about 1000° C., means for collecting and condensing vapor from said second heated zone to condensed liquid water and means for measuring the electrical impedance of at least a portion of said condensed liquid water.

6 Claims, 3 Drawing Sheets

PROCESS FOR MONITORING THE QUALITY OF WATER

This application is a division of application Ser. No. 07/138,757, filed Dec. 28, 1987, now U.S. Pat. No. 4,940,667.

BACKGROUND OF THE INVENTION

1. Field of the Invention

This invention pertains to apparatus for monitoring the quality of water, particularly (but not exclusively) the content of organic matter, for example volatile organics and volatile halogenated organics such as trihalomethanes. The desired quality of water depends of course on the intended end-use e.g. for drinking, pharmaceutical manufacture, intravenous uses, feed to high pressure boilers, rinsing of integrated circuits on semiconducting substrates and the like. One of the quality criteria is the content of organic matter, for example volatile organics including volatile halogenated organics such as trihalomethanes.

Sophisticated and expensive apparatus is available for measuring Total Organic Carbon content, Total Carbon Content, Total Oxygen Demand and the like on a more or less real-time basis (see below). Such apparatus is suitable for a municipal potable water treatment system or a centralized pure water treatment plant but much too expensive for monitoring the quality of water at distributed points of use, for example, potable water in the individual home, ultrapure water at a rinsing station in an integrated circuit production line, dialysis water in a decentralized hemodialysis facility and the like.

At present most municipal potable water treated systems do not thoroughly remove organics from water. Worse, the treatment systems used may produce organics which may be more noxious than those in the water before treatment. For example chlorine used as a disinfectant or to assist in coagulation and/or filtration frequently results in measurable amounts of trihalomethanes (THM's) in the potable water distributed. Ozone is sometimes substituted for at least part of the chlorine in a water treatment system. It does not produce THM's but in the quantities used does not degrade most organics present to carbon dioxide and water but rather to oxygenated organic compounds the physiological effects of which have been little studied. Further inadvertent cross connections between potable water distribution systems and sewage collection systems can introduce organics of household or industrial origin into potable water. Micro-and macro-organisms frequently live in "dead-ends" in potable water systems, avoiding thereby the effects of any residual chlorine in the potable water distribution system and contributing organics from the metabolism of various nutrients in the water. Further, many distribution systems contain plastic pipes from some varieties of which organics can be leached.

The public (becoming educated in the potential harmful effects of organics in distributed municipal potable water), is beginning to install at points of use in their homes devices such as activated carbon and/or reverse osmosis cartridges to remove organics at least partially. Such devices when new and in the absence of defects can remove 90 percent or more of organics from potable water. Some manufacturers include an inexpensive integrating flow meter to indicate on a more or less conservative basis when it is likely that the device should be replaced or rejuvenated. Such meter is of course useless if the device is defective, damaged or improperly installed or if the organic content of the potable water is substantially worse (in composition or concentration) than the manufacturer anticipated. Until now instruments for measuring the organic content of water in the individual home on a more or less real-time basis have been prohibitive in cost (as will be more fully discussed below).

Inexpensive methods are available for measuring organic content of water on a non-real-time basis. These include Chemical Oxygen Demand (boiling a sample of water with chromic and sulfuric acids and determining the quantity of chromic acid consumed) and Biological Oxygen Demand (determining the amount of oxygen used over some days by a bacterial culture injected into a closed sample of water and air. Neither of these are sufficiently sensitive at the concentrations of organics of interest in potable water e.g. 1 ppm or less. Further they require some training and sophistication on the part of the user, not generally available in a household.

A similar situation exists in a production line for integrated circuits on semi-conducting substrates. One would like to know on a real-time basis the quality of water at each of the many points of use. The available instruments for monitoring organics are far too expensive for such purpose. Such instruments are also too expensive for monitoring organics in the dialysis water in dispersed hemodialysis facilities.

It is therefore an objective of this invention to provide an apparatus which is feasible for monitoring the quality of water at points of use on an essentially real-time basis. Other objectives will become apparent from the disclosure and claims below.

2. Description of the Prior Art

Total Oxygen Demand ("TOD") Analyzer: This apparatus uses a furnace operating at about 900° C. and containing for example palladium or platinum wool or gauze. A stream of nitrogen, helium or argon carrier gas containing a low level of oxygen passes through the furnace. The oxygen content down-stream of the furnace is measured electrochemically, e.g. by a doped-zirconium oxide, high temperature oxygen concentration cell. From time to time a precise droplet of water is injected automatically or by manual syringe into the furnace and the depletion of oxygen in the carrier gas measured. The apparatus must be calibrated from time to time against a known standard sample. Such apparatus costs several thousand dollars.

Total Carbon Analyzer ("TCA"): This apparatus also uses typically a 900° C. furnace with noble-metal wool or gauze. The gas passing through the furnace may be air. The carbon dioxide content of the gas downstream of the furnace is measured by a non-dispersive infrared photometer. Again a precise droplet of water is injected from time-to-time into the furnace and the increase in carbon dioxide in the gas stream determined. This apparatus must also be calibrated from time-to-time against known samples.

Alternatively a persulfate salt (or other inorganic peroxide) is injected into a small stream of water which subsequently is highly irradiated with ultraviolet light. The carbon dioxide produced is stripped out of the water and measured by infrared photometry as discussed above.

Both of the above TCA apparatuses also cost several thousand dollars each.

Organic Carbon Analyzer (OCA or TOC): The TCA apparatus discussed above measures not only carbon dioxide from the oxidation of organic carbon compounds but also from bicarbonate ("inorganic carbon") which may be present in the water. OCA devices typically comprise TCA apparatus having a pretreatment section to remove bicarbonate, for example by acidifying and stripping with air. Such pretreatment may also remove volatile organic compounds ("VOC"'s) including THM's. OCA's are inherently more expensive than TCA's.

DESCRIPTION OF PREFERRED EMBODIMENTS

The present invention pertains to apparatus for monitoring the quality of water on an essentially real-time basis, said apparatus comprising a first heated zone, means for introducing at least a portion of said water into a said first heated zone and passing the vapor into and through a second heated zone, means for maintaining the temperature of said second heated zone to the range of from about 450° to about 1000° C., means for collecting and condensing water vapor from said second heated zone to condensed liquid water and means for measuring the electrical impedance of at least a portion of said condensed liquid water.

Figure 1:
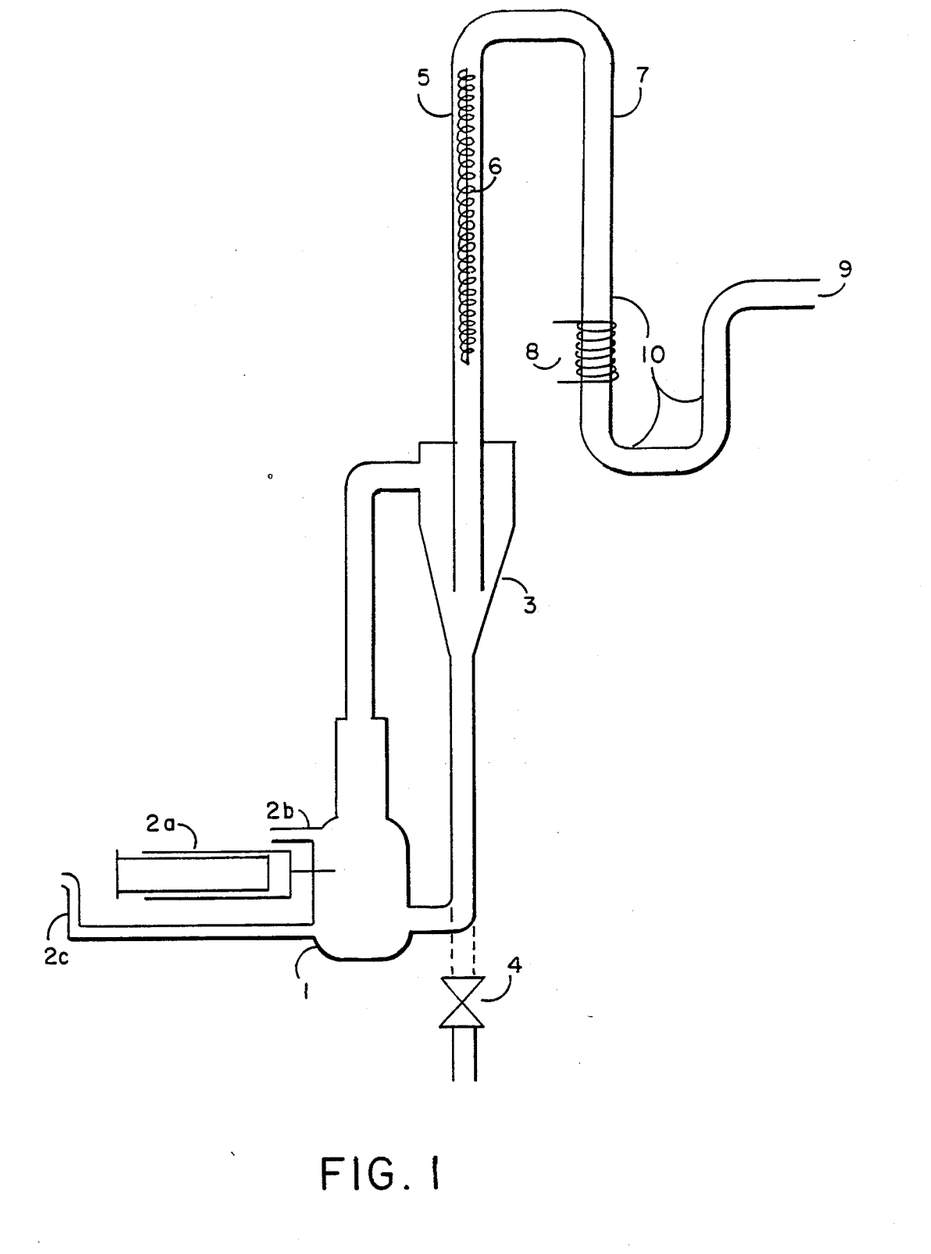
FIG. 1 is a schematic representation of a first preferred apparatus according to this invention.

Referring to FIG. 1 there is indicated schematically a preferred embodiment of the apparatus of this invention, in which 1 is a receiver and vaporizer for water introduced in discrete portions or continuously by feed means. The latter may be for example a manual or mechanical syringe 2a or simply an appropriate conduit typically containing flow restriction means. The water sample may also be introduced intermittently into vaporizer 1 by flowing water in tube 2b and overflowing out tube 2c, with the overflow tube positioned such by the preset height of overflow tube 2c) remains in the vaporizer 1 to be at least partially evaporated. The water overflow (prior to stopping the flow to allow the sample to heat to boiling) constitutes a rinse of the vaporizer chamber. The water that remains in tube 2c forms a seal to the air outside and prevents escape of vapors from the vaporizer. The apparatus of FIG. 1 is particularly indicated for water containing substantial amounts of inorganic electrolytes relative to the expected amounts of organic matter therein as will be more fully discussed below. In such case the water introduced into receiver 1 is quietly evaporated e.g. through gentle boiling by heating means not shown for the sake of clarity. Such means may be any known in the art, for example external electrical resistance heating, externally induced induction heating, internal electrical resistance heating including alternating current electrolytic heating between two or more internal electrodes.

The material of construction of receiver 1 may be any known in the art generally having a melting point substantially in excess of 100° C. and characterized by being substantially inert to boiling water. If the material is an electronic conductor such as copper, stainless steel or titanium then generally external electrical resistance heating or induction heating (using the material of the receiver itself as conductor) will be preferred. If the material is an electrical insulator such as pyrex, vycor, ceramic or a high temperature polymer (such as polyimidies, polyether sulfones and the like including filled and reinforced varieties) then any of the above mentioned methods of heating may be used.

Water and volatile organics are quietly vaporized out of receiver 1. If the water introduced into the vaporizer contains inorganic electrolytes substantial in amount compared to the organic content (as will be more fully discussed below) then it is desirable that droplets, mist or spray containing inorganic electrolyte are not carried through the apparatus. Mist eliminating means 3 may therefore be provided optionally. Means 3 may be vortex (passive centrifuge) mist eliminator as illustrated schematically, a plug of pyrex or glass wool, packed glass beads, baffles, or other mist eliminating devices well known in the art. Any liquid which separates out in the mist eliminating device may optionally be returned to the receiver 1 or drained out via valve 4.

Vapor from receiver 1 passes (with or without mist eliminator 3) into heated zone 5 maintained at a temperature in the range of from about 450° to 1000° C. wherein organic matter is oxidized and/or reformed according to the following generalized and typical equations:

(Trichloromethane) (1)

(Trichloromethane) (2)

(Carbon Tetrachloride) (3)

(Trichloroethylene) (4)

(Trichloroethylene) (5)

(Tetrachloroethylene) (6)

(Lindane) (7)

(Lindane) (8)

(Endrin or Dieldrin) (9)

(Endrin or Dieldrin) (10)

(Methoxychlor) (11)

-continued $$C_{16}H_{15}Cl_3O + 31H_2O \longrightarrow 16CO_2 + 3HCl + 37H_2 \quad (12)$$
(Methoxychlor)

$$C_3H_6O + 4.5O_2 \longrightarrow 3CO_2 + 3H_2O \quad (13)$$
(Acetone)

$$C_3H_6O + 5H_2O \longrightarrow 3CO_2 + 8H_2 \quad (14)$$
(Acetone)

$$C_2H_4O_2 + 2O_2 \longrightarrow 2CO_2 + 2H_2O \quad (15)$$
(Acetic Acid)

$$C_2H_4O_2 + 2H_2O \longrightarrow 2CO_2 + 4H_2 \quad (16)$$
(Acetic Acid)

$$CH_4O + 1.5O_2 \longrightarrow CO_2 + 2H_2O \quad (17)$$
(Methanol)

$$CH_4O + H_2O \longrightarrow CO_2 + 3H_2 \quad (18)$$
(Methanol)

$$C_2H_6O + 2.5O_2 \longrightarrow 2CO_2 + H_2O \quad (19)$$
(Ethanol)

$$C_2H_6O + 3H_2O \longrightarrow 2CO_2 + 6H_2 \quad (20)$$
(Ethanol)

$$C_2H_6O_2 + 2O_2 \longrightarrow 2CO_2 + 2H_2O \quad (21)$$
(Ethylene Glycol)

$$C_2H_6O_2 + 2H_2O \longrightarrow 2CO_2 + 5H_2 \quad (22)$$
(Ethylene Glycol)

$$C_6H_6 + 7.5O_2 \longrightarrow 6CO_2 + 3H_2O \quad (23)$$
(Benzene)

It is found that at temperatures below about 450° C. oxidation/reformation to carbon dioxide is often not sufficiently rapid and/or is incomplete. On the other hand at temperatures in excess of about 1000° C. it is found that carbon monoxide tends to be formed rather than carbon dioxide, the former decreasing the sensitivity of the apparatus as will become obvious from the further disclosure below. If water is introduced intermittently into receiver 1 then the second heating zone 5 may be partially cooled by vapor from said receiver. Such cooling is acceptable as long as the temperature remains within the cited range. The temperature of said heated zone 5 may deliberately be adjusted to be in excess of 1000° C. by an amount such that the intermittent flow of vapor from receiver 1 brings the temperature within the cited range.

It is found that the rate of oxidation/reformation is increased by an extended surface area 6 in heated zone 5. Such extended area 6 may take the form as illustrated of a closed or open coil of metal, quartz or other material having a melting point above the temperature of heated zone 5, or of one or more wires, ribbons or filaments, metal gauze, quartz or ceramic grains, beads, saddles, coils or other structures. Zone 5 may be heated by external resistance heating.

Alternately if the wall of zone 5 is an electrical conductor or semiconductor in the temperature range of from about 450° to about 1000° C. then the zone may be heated by inductive heating or by direct electrical resistance heating (i.e. by passing an electric current through said wall from substantially one end of heated zone 5 to the other. If extended surface area 6 is electrically conducting or semi-conducting in the temperature range from about 450° to about 1000° C. then such surface area itself may be inductively heated from an external source. If such surface area is as well substantially continuous and/or interconnected (as for example one or more ribbons or coils of appropriate metal, juxtaposed pieces of metal gauze, metal wool, a body of granules, beads, saddles and other structures of metal or other materials which are conducting or semi-conducting in the cited temperature range) then such area may be heated directly by electrical resistance heating, electrical connections being made through the wall of the heated zone at substantially each end of said heated zone 5. Suitable metals and alloys for electrical resistance heating include:

80-20 Ni-Cr
80-20 Ni-Cr+Al
60-15-25 Ni-Cr-Fe
50-18-32 Ni-Cr-Fe
37-18-43-2 Ni-Cr-Fe-Si
72-22-4 Fe-Cr Al
72-22-4 Fe-Cr-Al+Co
Pt
90-10 Pt-Ir
60-40 Pt-Rh
Ta
Mo Si$_2$

It will be obvious that the surfaces of the material of construction of zone 5 and of the optional extended surface area 6 which are in contact with vapor from receiver 1 should not react with such water vapor at the temperature of heated zone 5 to produce carbon dioxide or volatile materials which are electrical conductors when dissolved in water. Thus for example such surfaces preferably should not be graphite or carbides.

Vapor containing oxidized/reformed organic products from heating means 5 is cooled and condensed in condensing means 7 to approximately room temperature. Condensing means 7 may be cooled for example by natural or forced convection air or by water. If water is introduced on an intermittent basis into receiver 1 then condensing means 7 may have a substantial heat capacity in order to rapidly absorb intermittent heat loads. Condensing means 7 may contain extended surface area (not indicated in the figure) to assist in cooling and condensation, such extended area being similar in structure to extended area 6 which is suitable for heating means 5.

Condensed water (containing dissolved products of the oxidation/reformation of organic compounds in heating means 5) is accumulated in condensate receiver 10 which may take any suitable form. The electrical impedance of the condensed water is determined by impedance measuring means 8. Such means may be any electrodeless impedance (conduction) measuring device well known in the art. For example it may take the form of an external coil, the alternating current impedance of which depends upon the impedance of the condensed water in condensate receiver 10. In such case the material of construction of condensate receiver 10 at least in the vicinity of means 8 should be a low electrical loss material, generally a dielectric, typically glass, pyrex, vycor, di-electric ceramics, plastics such as polypropylene, polystyrene, or Teflon. Impedance measuring means 8 may also, for example, take the form of two or more electrodes in contact with condensed water in receiver 10. Many forms of such electrodes are suitable. For example the electrodes may comprise a pair of wires spaced apart, each at a cross-section of receiver 10. Alternatively one electrode may be the wall of receiver 10 or a portion of said wall, the second electrode (electrically insulated from the first electrode) immersed in the condensed water in receiver 10. As yet another example, each electrode may be a portion of the wall of receiver 10, each portion electrically insulated from the other. Many other impedance measuring structures will be obvious to those skilled in the art of measuring the electrical impedance of liquid water.

As water is collected in condensate receiver 10, excess leaves receiver 10 through any suitable exit means 9.

The electrical impedance of the condensed water in receiver 10 depends upon the nature and quantity of dissolved and/or dispersed substances in the water introduced into receiver 1. If the apparatus is operated as described above, then dissolved non-volatile minerals such as sodium chloride and calcium sulfate will remain in receiver 1. Bicarbonate minerals such as calcium bicarbonate will tend to release carbon dioxide which, dissolving in the water condensed in condensate receiver 10 will decrease the electrical impedance of such water. The contribution of carbon dioxide released from bicarbonate minerals to the electrical impedance of water collected in receiver 10 may be determined by processing a portion of water in the apparatus while the temperature of the heating means 5 is maintained below oxidation/reformation temperatures.

Non-volatile organics will also remain in receiver 1 though heat sensitive substances may at least in part be decomposed into volatile substances, depending of course on the temperature of receiver 1.

Volatile organics in water introduced into receiver 1 will in general be oxidized/reformed by heating means 5 at least in part into water soluble substances which will reduce the electrical impedance of condensed water collected in condensate receiver means 10. For example, in accordance with equations (1) and (2) above, trichloromethane will result in carbon dioxide and hydrogen chloride. Both of the latter products are soluble in water forming carbonic acid and hydrochloric acid respectively. Carbonic acid is only weakly ionized in water at room temperature but hydrochloric acid is strongly dissociated into negatively charged chloride anions and highly conducting positively charged hydrogen ions. In this case the electrical impedance of condensed water collected in receiver 10 will be determined primarily by the hydrogen chloride produced; the greater the amount of trichloromethane in the water introduced into receiver 1, the smaller will be the impedance of water collected in receiver 10.

For purposes of illustration if one assumes that the water monitored contains 1.6 ppm organics as carbon, that the portion analyzed is completely vaporized and that the carbon therein is completely oxidized by reforming without added air or oxygen according to the equation:

$$C + 2H_2O \rightarrow CO_2 + 2H_2 \qquad (24).$$

then the concentration in terms of $CO_2$ is $44/12 \times 1.6$ ppm = 5.9 ppm in the reformed vapor portion. If the $CO_2$ formed is condensed in the same proportion as the vapor, its electrical conductivity would be approximately 2 to 3 microSiemens/cm at ambient temperature. This is equivalent to a sodium chloride solution having a concentration of about 1 to 1.5 milligrams per liter. Of course, the concentration and conductivity of $CO_2$ in the condensed water will be affected by the temperature of the condensate, the degree of absorption of $CO_2$ in the condensing water, and by the relative volatility of the organics in the sample fed to receiver 1, as will be more fully disclosed below. Since one would prefer that the impedance measuring means 8 in FIG. 1 not have to detect small differences beteween large numbers (the reciprocals of the conductivities), the condensed water should not have more than about 1 milligram per liter of total dissolved solids. This latter observation illustrates the importance of quiet evaporation in receiver 1 of FIG. 1 and/or of good demisting in demisting means 3 of said figure to avoid entrainment and carryover of dissolved salts from the sample in receiver 1 into the impedance measuring means 8. As will be more fully disclosed below, other means may be used to assure low total dissolved solids in the condensed water portion whenever such is necessary. On the other hand when the apparatus of this invention is used for example for monitoring the organic content at point of use of ultrapure water used for rinsing integrated circuits on semiconductors such precautions are not generally required since acceptable ultrapure water in such application clearly has a conductivity as low as 0.06 microSiemens/cm.

The above comments apply to organics which have essentially the same volatility as water (or to apparatus according to this invention in which water is continuously fed to receiver 1 of FIG. 1) and to equilibrium relationships. If the organics have a volatility greater than that of water and if water is fed intermittently to receiver 1 then the sensitivity of the apparatus will be increased by a "first-vapor" effect, i.e. the first vapor from receiver 1 will be richer in volatile organics than the average vapor and the first condensate in receiver 10 of FIG. 1 richer in dissolved carbon dioxide (and therefore higher in conductivity) than the average condensate.

The first vapor effect is particularly important in the case of water treatment systems which use activated carbon to remove organics (e.g. home water systems and ultrapure water systems) since generally the first organics to break through such sorbent have volatilities greater than that of water. Organics passing through a reverse osmosis membrane (commonly used in home, medical, pharmaceutical and ultrapure water systems) also tend to be more volatile than water.

Volatile organic compounds (VOC's), especially halogenated hyrdocarbons, are particularly important in water intended for drinking, hemodialysis and rinsing of integrated circuits on semiconductors. For example if the organic carbon is present as chloroform, a common trihalomethane (THM), then for every milligram of carbon as carbon, 9 milligrams of HCl are formed (see equations (1) and (2) above). HCl is of course very soluble and completely ionized in water. The change in conductivity of the water condensed in receiver 10 (of FIG. 1) will be about 90 microsiemens/cm (on the average i.e. not taking into account the first vapor effect) for every milligram per liter of carbon present as chloroform, corresponding to the conductivity of about 50 milligrams per liter of sodium chloride. The apparatus of this invention is therefore particularly useful in monitoring volatile halocarbons, the latter being particularly undesirable in water for most end users.

Figure 2:
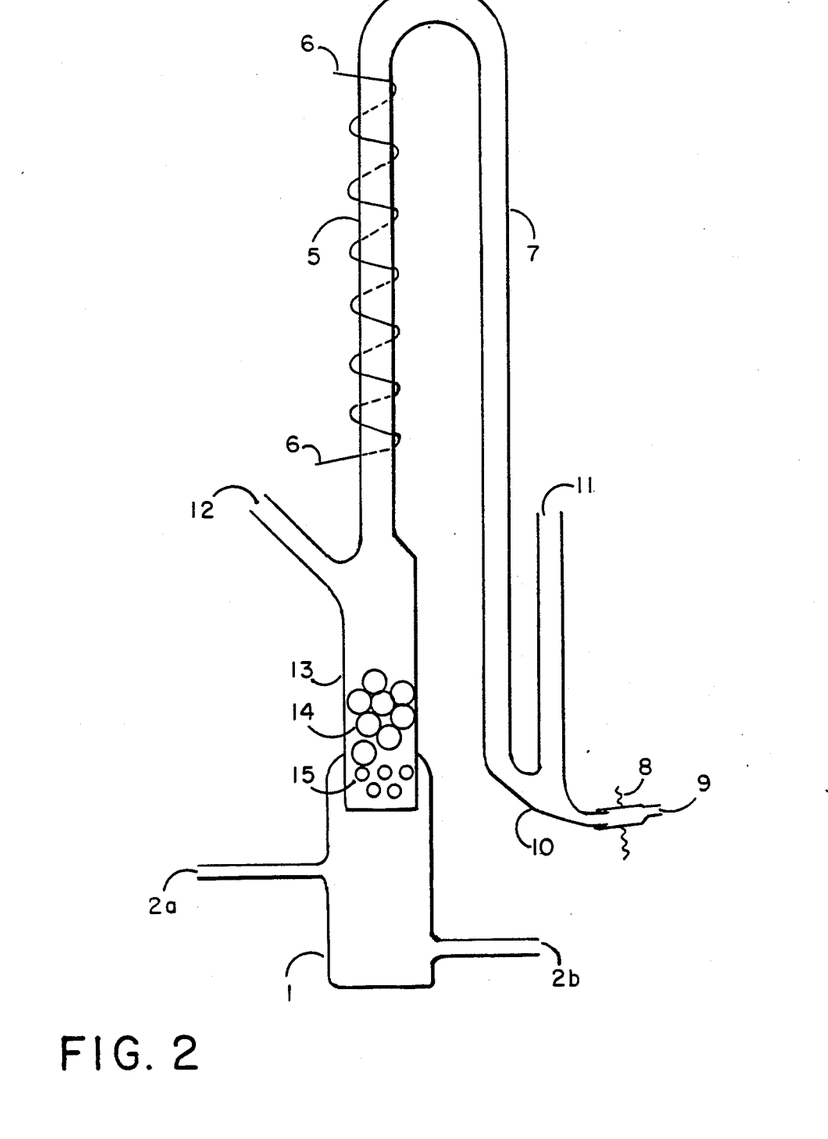
FIG. 2 is a schematic representation of a second preferred apparatus according to this invention.

Referring to FIG. 2 there is indicated schematically a second preferred embodiment of the apparatus of this invention prepared from in whole or in part of commercial quartz, vitreous silica (such as Rotosil, T-08, Heralux, Optasil, Herasil, Ultrasil, Suprasil (Anersil/Heraeus), Vitreosil (Thermal American and Thermal Syndicate Ltd)), pyroceram, alumina (84 to 100%), mullite or porcelain. Chamber 1 is a receiver typically having a diameter of about 11 to 12 millimeters and a height of from about 37 to about 50 millimeters. Receiver 1 is conveniently wrapped in 0.125 millimeter Nichrome wire held in place with a high temperature ceramic adhesive such as Ceramabond 569 or 603 (made by Aremco Products, Inc. U.S.A.).

Water may be introduced into receiver 1 continuously or intermittently in discrete portions by quartz tube means 2a and/or 2b which may for example have inside diameters of 2 to 4 millimeters. The use of two such means permits convenient cleaning and rinsing of receiver 1, for example by the intermittent flushing and filling previously described for FIG. 1. Vapor from receiver 1 passes into chamber 13, which serves the dual purpose of mist eliminator and partial condenser. Chamber 13 protrudes into receiver 1 and has openings 15 to allow the vapor to enter the chamber, while minimizing the chances for liquid to be entrained in case of bumping during evaporation. Any condensate which forms in chamber 13 will flow back into receiver 1 through openings 15. Partial condensation of vapor caused by cooling at the walls of chamber 13 enriches the concentration of volatiles in the vapor passing from chamber 13 into heated zone 5 and further enhances the first vapor effect. Chamber 13 may be at least partly filled with suitable packing such as glass beads 14 to encourage good contact between refluxing partial condensate and vapor rising from receiver 1 toward heated zone 5. The beads may be introduced through opening 12, which would then be closed during operation of the device. It has been found that some water condenses from the vapor as a result of cooling st the walls of chamber 13 and as it flows downward countercurrent to the ascending vapor results in enrichment of the volatile components, and scrubbing of the mist that may form in case of less than gentle evaporation in receiver 1. Zone 5 for example may comprise 6 to 7 mm quartz tubing. Said zone is heated by a Nichrome wire 6 which may be for example 0.125 mm in diameter and approximately 250 mm long wrapped around heated zone 5 and held in place with Ceramabond referred to above. Heated zone 5 may be insulated with appropriate insulating material, for example Fiberfax brand mineral fibers. The temperature of the heated zone may be measured for example with thermistors or optically. For purposes of this invention it is convenient to use the following guidelines:

| Color | Temperature |
| --- | --- |
| Incipient Red Heat | 500 to 550° C. |
| Dark Red Heat | 650 to 750° C. |
| Bright Red Heat | 850 to 950° C. |

Condensing means 7 may also be 6 to 7 millimeter commercial quartz tubing cooled by natural or forced convection with air. Extended surface in means 7 may for example consist of a number of glass beads. Condensate receiver means 10 communicates with impedance measuring means 8 which may conveniently be a Radiometer Copenhagen CDC 314 flow and pipette conductivity cell having a cell constant of about $3.16 \text{ cm}^{-1}$ and a volume of about 0.4 mil (Radiometer, Copenhagen, Denmark). Condensed water flows from condensate receiver 10 through the conductivity cell 8 and leaves the device of FIG. 2 through means 9. Vent means 11 may be provided to dampen flow oscillations in the device.

To illustrate the use of the apparatus of FIG. 2, means 6 is heated to dark red heat and receiver 1 is heated at such a rate that the evaporation rate is equivalent to about one drop of water every half minute. When the water fed to receiver 1 is an ultrapure water typical of that used in electronic component washing it is found that the impedance of the condensate collected in condensate receiver 10 is about 500,000 to 1,000,000 ohm cm. On the other hand when such ultrapure water has about 0.8 ppm of chloroform added the impedance of the condensate is found to be less than 20,000 ohm cm. Quiet boiling in receiver 1 can be assisted by use of boiling chips for example glass beads (3/32") or other structures which promote nucleated boiling.

Figure 3:
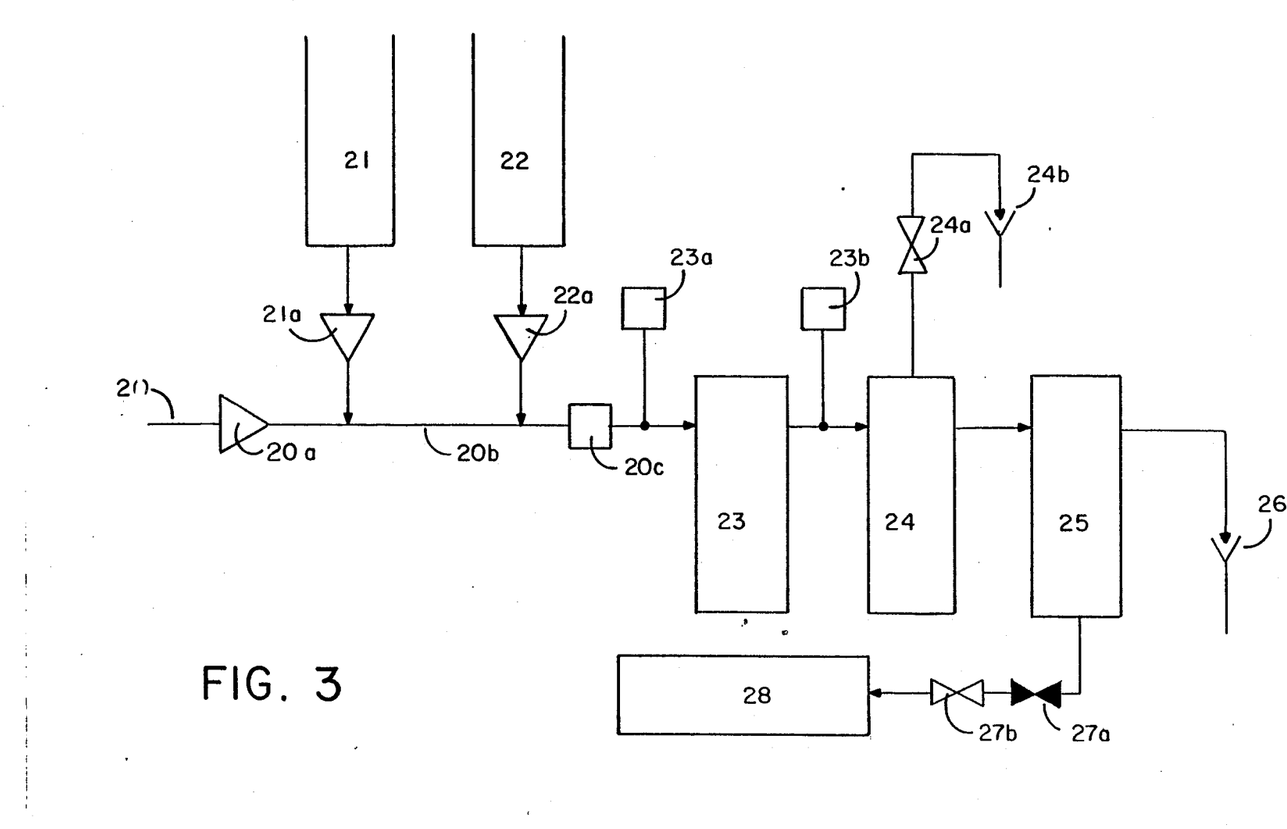
FIG. 3 is a schematic representation of an apparatus adapted to remove at least in part organics from water and comprising an instrument in accordance with this invention for monitoring the quality and controlling the flow of effluent water from said apparatus.

Referring to FIG. 3 there is indicated schematically an apparatus adapted to remove at least in part organics from water and comprising an instrument according to this invention for monitoring the quality of effluent water from said apparatus. In the drawing 20 represents a source of demineralized water having essentially non-detectable organic content. The constant displacement pump 20a has a capacity of about 15 ml/min. Reservoir 21 contains demineralized water having about 7 micrograms of chloroform per ml prepared by diluting a stock solution of demineralized water saturated in chloroform (about 7 mg/ml) 1 to 1000 with demineralized water. Positive displacement pump 21a is adjusted to add about 1.9 ml/min of chloroform containing water to conduit 20b. Reservoir 22 contains demineralized water having about 3 mg sodium chloride per ml, prepared by diluting a stock solution of demineralized water saturated in sodium chloride 1 to 100 with demineralized water. Positive displacement pump 22a is adjusted to add about 1.9 ml of salt containing water to conduit 20b. The mixture of salt, water and chloroform passes to a cavity 20c containing a magnetic stirrer to homogenize the mixture which then passes to cartridge filter 23 having a rating of about 10 micrometers. Pressure gauges 23a and b monitor pressure loss through cartridge filter 23 which is changed whenever the loss attains 1 bar. 24 represents a spiral wound reverse osmosis cartridge comprising low-pressure cellulose acetate film. The effective membrane area is about 2500 cm² and the core of the cartridge contains about 100 ml of activated carbon, permeate from the membrane entering one end of the core and leaving from the other. Permeate passes to product holding reservoir 25. Valve 24a is adjusted to permit about 3.8 ml/min of non-permeate to flow to drain 24b. Pressure at gauge 23b is maintained at about 4 bars by an automatic pressure regulating valve (not shown). Excess product water overflows reservoir 25 to drain 26. About once an hour a sample of product water is admitted from reservoir 25 to water quality monitor 28 through solenoid valve 27a and flow control restrictor 27b. Valve 27a is controlled by a timer such that approximately 30 ml is flowed through receiver 1, referring to FIG. 2, and the overflow 2b is adjusted such that a 10 ml sample remains in receiver 1. Water quality monitor 28 is similar to that described in connection with FIG. 2. Referring to the latter, the procedure is as follows: Heating zone 5 is first maintained at a temperature substantially less than 450° C. and water is evaporated from reservoir 1 and condensate water is directed by gravity from reservoir 10 to conductivity cell 8. The condensate hold-up volume in reservoir 10 is only a few drops. The electrical impedance of the first condensate is measured by conductivity cell 8. Heating zone 5 is then heated to the range of from about 450° to about 1000° C., a second sample of water is evaporated from reservoir 1 and the first condensate is collected and the impedance measured. For several weeks it is found that the impedance measurements of the two samples are essentially the same. To simulate breakthrough of cartridge 24, water is collected at 23b and analyzed as above. It is found that the second sample of such simulated breakthrough (that is the condensate collected when heated zone 5 has a temperature in the range of from about 450° to about 1000° C.) has about half the electric impedance of the sample of condensate collected when the heated zone 5 has a temperature substantially below 450° C.

Although not shown, means well known may be provided for automatically generating an audio or video signal when the quality of the product water is below specification as determined by the monitoring instrument. Further means may then be employed for automatically shutting off the water treatment apparatus and/or bypassing the off-spec. product water from the water product reservoir based on the generated signals.

EXAMPLES

Example 1

Ten ml of demineralized water was injected into receiver 1 of the organic monitor described in FIG. 2, with no glass beads or other packing in the demister/reflux zone 13. Receiver 1 was heated electrically by Nichrome wire wrapped around the chamber at a heat input of approximately watts. Zone 5 was likewise heated electrically by Nichrome wire 6 at a heat input of approximately 35 watts. Zone 5 was insulated by mineral wool (Fiberfax) such that the zone was red hot. A maximum reading of 1.4 microSiemens/cm was read by the conductivity cell 8 approximately fifteen minutes after injection of the sample. The experiment ass repeated except that zone 5 was heated at approximately 8 watts, at which setting it did not reach incipient red heat. A similar conductivity reading was recorded, indicating no gain in any conductive species upon pyrolysis at red heat.

Example 2

The experiment in Example 1 was repeated with demineralized water to which was added chloroform to a concentration of approximately 8 micrograms per liter (ppb). With zone 5 red hot a reading of approximately 2 microSiemens/cm was read, while below red heat the reading was about 1.4.

Example 3

The experiment in Example 2 was repeated with a water sample containing approximately 75 ppb chloroform. With zone 5 red hot the maximum reading was about 8 microSiemens/cm, whereas below red heat the maximum reading was about 1.6.

Example 4

The experiment was repeated with approximately 115 ppb acetone in the water. Maximum conductivity readings of about 2 and 1.6 were obtained respectively for red hot zone 5 (Pyrolysis mode) and 1.6 below incipient red heat (nonpyrolysis mode).

With approximately 1100 ppb acetone the maximum conductivity readings were about 5 and 2 respectively, and with 2300 ppb the conductivity readings were about 9 and 1.8, respectively.

In all of the above examples only a small fraction of the sample had been vaporized when the peak condensate conductivity was observed, confirming the "first vapor" effect on both the chloroform and the acetone.

Example 5

The experiment in Example 3 was repeated, but with the demister/reflux zone 13 filled with 3/16" glass beads. During vaporization of the sample, water was observed partially condensing in the demister/reflux zone and occasionally dripping back into receiver 1. The maximum conductivity readings observed were approximately twice as high as had been measured on Example 3, where no beads were present in zone 13, proving the sensitivity enhancement effect from the reflux zone 13 on the "first vapor" effect.

Example 6

The experiment in Example 1 was repeated, using demineralized water to which sodium chloride wss added to a concentration of 200 milligrams per liter (ppm). There was no noticeable difference in the condensate conductivity measurements between this experiment and Example 1 (demineralized water), proving that no significant extrainment or carryover of salt occurred.

While the invention has been described with respect to certain exemplifications and embodiments thereof, the scope is not to be so limited except as in the claims appended hereto.

We claim:

1. A process for monitoring volatile organic compounds in water comprising gently boiling at least part of a first portion of said water containing volatile organic compounds into a heated zone while maintaining the temperature of said zone substantially less than 450 °C., collecting and condensing at least part of the first portion of water vapor from said zone into a first condensed liquid water sample and measuring the electrical impedance of said first condensed liquid water sample thereby obtaining a first impedance measurement, subsequently gently boiling at least part of a second portion of said water into said zone while maintaining the temperature in said zone in the range of from about 450° to about 1000° C., whereby reformable and/or oxidizable volatile organic compounds in said water are reformed and/or oxidized at least in part into second compounds volatile in said temperature range which second compounds are at least partially soluble in water and at least partially ionizable therein, collecting and condensing at least part of the second portion of water vapor from said zone into a second condensed liquid water sample measuring the electrical impedance of said second condensed liquid water sample thereby obtaining a second impedance measurement and comparing said first and second impedance measurements to determine the volatile organic content of said water.

2. A process for monitoring volatile organics contained in water comprising boiling at least part of a first sample of said water containing volatile organic compounds in a first heated zone while maintaining said first zone at a temperature which is not sufficient to oxidize and/or reform said volatile organics, collecting and condensing at least part of the resulting vapor from the said first sample from the said first heated zone into a first liquid water sample and measuring the electrical impedance of said first liquid water sample thereby obtaining a first impedance measurement, boiling at least part of a second sample of said water in a first heated zone while maintaining said first zone at a temperature which is not sufficient to oxidize and/or reform said volatile organics, passing into a second heated zone at least part of the resulting water vapor from said first zone while maintaining said second heated zone at a temperature sufficient to oxidize and/or reform said volatile organics into water soluble, electrically conducting substances, collecting and condensing at least part of the resulting vapor from the second sample of said water from the second heated zone into a second liquid water sample and measuring the electrical impedance of said second liquid water sample thereby obtaining a second impedance measurement and comparing said first and second impedance measurements to determine the volatile organic content of said water.

3. The process of claim 2 wherein the first heated zone is maintained at a water vaporizing temperature which is substantially below 450° C.

4. The process of claim 2 wherein the second heated zone is maintained at a temperature from about between 450° C.–1000° C.

5. The process of claim 2 wherein the first heated zone is gently boiled and maintained at a temperature sufficient to vaporize off water and volatile organics so as to enrich the resulting water vapor in volatile organics while simultaneously allowing dissolved, non-volatile, conductive salts to be substantially retained in said first heated zone.

6. The process of claim 2 wherein said impedance measurements are taken continuously during the process of monitoring said volatile organics.

* * * * *

UNITED STATES PATENT AND TRADEMARK OFFICE
CERTIFICATE OF CORRECTION

PATENT NO. : 4,977,094

DATED : Dec. 11. 1990

INVENTOR(S) : Arthur L. Goldstein and Edgardo J. Parsi

It is certified that error appears in the above-identified patent and that said Letters Patent is hereby corrected as shown below:

On the title page, item [75], "Arthur J. Goldstein" should be
--Arthur L. Goldstein--.

Signed and Sealed this

Seventeenth Day of September, 1991

*Attest:*

HARRY F. MANBECK. JR.

*Attesting Officer*  *Commissioner of Patents and Trademarks*